(12) United States Patent
Wiedenbein (10) Patent No.: US 8,409,229 B2
(45) Date of Patent: Apr. 2, 2013

(54) SURGICAL INSTRUMENT

(75) Inventor: Wolfgang Wiedenbein, Seelze (DE)

(73) Assignee: Cardiomedical GmbH, Langenhagen (DE)

( * ) Notice: Subject to any disclaimer, the term of this patent is extended or adjusted under 35 U.S.C. 154(b) by 264 days.

(21) Appl. No.: 12/728,834

(22) Filed: Mar. 22, 2010

(65) Prior Publication Data

US 2011/0152903 A1    Jun. 23, 2011

(30) Foreign Application Priority Data

Dec. 17, 2009    (EP) ..................................... 09015641

(51) Int. Cl.
*A61B 17/08* (2006.01)
(52) U.S. Cl. ...................................... 606/158
(58) Field of Classification Search .................. 606/157, 606/158
See application file for complete search history.

(56) References Cited

U.S. PATENT DOCUMENTS

| | | | |
|---|---|---|---|
| 2,668,538 A | 2/1954 | Baker | |
| 3,608,554 A | 9/1971 | McGuinness | |
| 3,911,766 A | 10/1975 | Fridolph et al. | |
| 3,952,749 A | 4/1976 | Fridolph et al. | |
| 4,192,314 A | 3/1980 | Curutchet | |
| 5,792,177 A | 8/1998 | Kaseda | |
| 6,692,514 B2 | 2/2004 | Fogarty et al. | |
| 6,719,766 B1 | 4/2004 | Buelna et al. | |
| 7,588,585 B2 * | 9/2009 | Gold et al. | ................ 606/206 |
| 2003/0212435 A1 | 11/2003 | Gold et al. | |
| 2005/0059987 A1 | 3/2005 | Hermann et al. | |

FOREIGN PATENT DOCUMENTS

| | | |
|---|---|---|
| DE | 2060814 A | 6/1971 |
| DE | 2521487 C2 | 11/1975 |
| DE | 2747625 A1 | 10/1976 |
| DE | 69632451 T2 | 10/1997 |
| DE | 202007016057 U1 | 1/2008 |

* cited by examiner

*Primary Examiner* — Melanie Tyson
(74) *Attorney, Agent, or Firm* — Husch Blackwell LLP; H. Frederick Rusche; Robert C. Haldiman (57) ABSTRACT

A vascular clamp, has an operating mechanism, and an actuating tool. The vascular clamp is grasped using a detachable operating mechanism, wherein an actuating tool that can be slid in and out is able to open and close the jaws of the grasped vascular clamp. The vascular clamp includes a coupling arrangement and a continuously adjustable adjustment mechanism for this purpose. In order to grasp the vascular clamp, the operating mechanism includes a gripping mechanism and is equipped with a locking mechanism, which are used to create a detachable connection between the vascular clamp and the operating mechanism. For stepless opening and closing, the actuating tool engages in the adjustment mechanism of the vascular clamp and opens and closes the jaws of the vascular clamp by corresponding rotation of the actuating tool. The surgical instrument according to the invention is disassemblable and reassemblable, and can advantageously be disassembled into its three constituent parts during an operation, thus keeping the access opening in the chest free from obstructing instruments.

13 Claims, 4 Drawing Sheets

SURGICAL INSTRUMENT

BACKGROUND OF THE INVENTION

1. Technical Area

The present invention relates generally to the area of medicine, particularly surgery. In surgery, instruments, devices or methods are used for examining the insides of living organisms and/or o for carrying out surgical operations. Surgical instruments include all those medical instruments that are used primarily in surgery. These also include instruments for ligating or otherwise compressing tubelike or vasiform body parts, preferably blood vessels. Surgical instruments of such kind are categorized as gripping or clamping instruments, of which many different kinds already exist, and they are sufficiently known. Gripping or clamping instruments are used for example in heart, chest and vascular surgery. In heart and chest surgery, the operation carried out is usually open, in which access to the heart is gained by opening up the chest. Access is usually gained with a median sternotomy, wherein a longitudinal incision of approximately 25 cm is usually made through the sternum. The longitudinal incision is necessary to open the ribcage. For a thoracotomy, the chest is opened surgically with an intercostal incision, that is to say a small incision in the space between the ribs. The opening created by the sternotomy or thoracotomy is kept free with a rib spreader, an instrument for parting the ribcage and keeping it open. This opening is used by the surgeon to gain access for surgical operations. Operations on organic body parts may then be carried out through the opening created in the ribcage with a wide variety of other surgical instruments. For example, once the patient's heart is exposed various catheters, cannulas and clamps can be inserted in and attached directly to the heart and the large blood vessels. Typically, the aorta is occluded by placing a vascular clamp round the rising aorta to isolate the coronary arteries from the rest of the arterial system. The surgical instruments that are essential for doing this not only reduce the size of the opening, thereby obstructing the surgeon's activity and field of vision, but also render rapid healing less likely because of the size of the opening needed, the tissue damage this causes, and the trauma caused by the surgical operation itself.

2. Background in the Related Art

The present invention relates to such a medical instrument, particularly a surgical instrument, for example a vascular clamp for occluding tubelike, organic, human or animal body parts such as blood vessels, preferably arteries, consisting of two movable shanks that are connected to each other in scissor-like manner, and having a working part, preferably a clamping and gripping mechanism consisting of two gripping elements at the distal end, and having an actuating mechanism, preferably a handle device with two annular handle parts at the proximal end, and includes a locking mechanism close to the annular handle parts and preferably including two ratchets with detent teeth, which locking mechanism may be used to adjust the gripping elements to one of several locked positions.

Medical instruments of such kind, particularly gripping and clamping surgical instruments of various constructions and designs, have proven their usefulness in surgery many times over, and are known from the prior art.

One known example is the Kocher clamp. The Kocher clamp is a trauma clamp and belongs to the class of grasping surgical instruments. A clamp of this kind is most often used when structures must above all be gripped and held securely, and constricted at the same time. For this purpose, the Kocher clamp has serrated jaws, so that the tissue that is being gripped does not slip forwards from between the jaws.

The curved aortic clamp according to the design by Huland and Noldus is also known, this being inserted between the rectum and the Denonvilliers' fascia in preparation for prostatectomies, to prevent injury to the rectum.

The serration on the jaws of this instrument has already been disclosed by its inventor in U.S. Pat. No. 2,668,538. However, the disadvantage of these instruments is that they do not completely prevent tissue damage.

One such surgical clamp, from the wide variety of such instruments, is described in German Patent No. DE 27 47 625 A1. The handle on this clamp was specifically modified, German Patent No. DE 25 21 4878 C2 illustrates that the claws are curved. In this context, the surgical clamp described in German Patent No. DE 2 060 814 A may be considered as representative of the many different clamp types. The disclosed clamp enables clamping to be carried out safely and securely without the use of sharp edges, thus preventing inadvertent injury to sensitive tissue. Each jaw has at least one lengthwise ridge with a row of teeth, and at least one longitudinal groove to accommodate the teeth in the lengthwise ridge on the opposing jaw. The teeth on the ridges of the associated jaw are offset laterally relative to each other, and the ridges on the associated jaws have flanks extending lengthwise that fit closely together in the clamping position, and are shaped to form a pocket extending lengthwise to accommodate tissue, with a middle section having an enlarged cross section and reduced end sections.

The process of disconnecting blood vessels with the surgical instruments described earlier is carried out according to the same principle. The two jaws of the surgical instruments are moved closer to and farther away from each other using annular handles. A latching or locking mechanism, with which the jaws can be set in one of several different positions, is arranged on the scissor-like elements. One ratchet and teeth cooperating therewith are located on each of the scissor-like elements, or toothed racks with detent teeth as a locking mechanism are arranged on the scissor-like elements. Consequently, the distance between the jaws may only be adjusted incrementally. The major disadvantage of such graduated movement is that the vessel is clamped either too tightly or too loosely.

Another embodiment of an aortic clamp is shown in the "HORIZON" product catalogue issued by Cardiomedical GmbH, on the homepage under Cardio Vision on the MIC Accessories page together with an illustration. The aortic clamp described in the product catalogue is also shown in general in German Patent No. DE 696 32 451 T2, FIG. 4.

In order to avoid the disadvantages of the scissor-like clamps designed with annular handles, and those of the ratchet with detent teeth to form a locking mechanism, German Patent No. DE 20 2007 016 057 U1 suggests a stepless adjustment of the gripping elements for a laparoscopic aortic clamp. Aortic clamps with continuous adjustment of the gripping elements or the jaws may also be seen on the homepage of www.eisold-instruments.com, on the "Aortic clamps" tab under Products.

The most closely related art is considered to be the object of US Patent No. 2003/0212435 A1. According to paragraphs 2, 30 and FIG. 6 in the published document, the object disclosed relates to a surgical instrument that may be disassembled and reassembled, consisting of an operating mechanism, a continuously adjustable gripping and clamping vascular clamp having a body element, a working part, an adjustment mechanism, a coupling arrangement and an actuating tool, which is connected in fixed manner to the operating mechanism.

All of the surgical instruments described in the preceding are similar in respect of their size, their scissor-like form, and usually annular handles for operating the jaws, and a typical locking device.

The most recent developments in heart, chest, and vascular surgery, which indicate a trend towards minimally invasive surgery, are reducing the size of the access opening in the chest, particularly for a thoracotomy, in order to minimize tissue damage and operative trauma to the patient, and to help accelerate the healing process. The drawback of small access openings from the surgeon's point of view is that surgical instruments that must be inserted in such an opening significantly reduce the surgeon's operating area and field of vision, which makes it more difficult to perform the operation.

Accordingly, the movement towards minimally invasive surgery can only be realized successfully if the surgical instruments used are adapted to satisfy the new requirements, the smaller access openings. In other words, the current designs of surgical clamps no longer satisfy medical requirements for surgical operations. In order to reduce the patient's stress and minimize the risk of adverse effects, operations are also performed more rapidly. For this, atraumatic instruments are needed, designed in such a way that their handling makes surgical operations considerably easier.

These purposes are satisfied in part by the object disclosed in US Patent No. 2003/0212435 A1. The object relates to a surgical clamp that may be disassembled and reassembled. Because it may be disassembled, it satisfies the requirement for smaller instruments for use in minimally invasive surgery. The disadvantage of this disassemblable surgical clamp, however, is that it does not satisfy the criterion of optimal handling during an operation.

The task of the present invention is therefore to provide a medical instrument of the type described in the introduction, for use in surgery, which has none of the disadvantages and inadequacies of the known devices as described above, and to offer a technical solution for producing a surgical instrument having simple functional geometry that satisfies these more stringent requirements. The surgical instrument should have the same properties as the surgical clamps according to the related art, as well as superior handling, and at the same time provide for a larger, not a smaller, operating and viewing field for the surgeon.

These problems are solved according to the invention by the characterizing features of claim 1. Advantageous embodiments and improvements of the invention are described in the subsequent, dependent claims and the following descriptions.

DESCRIPTION OF THE INVENTION

In order to provide a medical instrument having these features of the present invention, particularly an instrument for use in surgical operations on human and animal bodies, in surgery, it is suggested according to the invention to construct the surgical instrument such that the surgeon has an ergonomically designed operating mechanism that makes handling the surgical instrument, particularly a vascular clamp, significantly easier. In order to create a surgical instrument of such design, it was first necessary to solve the problems described in the preceding. The solution to these problems consists in replacing the previously known surgical instruments, with their scissor-like action, annular handles and incremental locking mechanism, with a surgical instrument according to the invention.

To this end, it was suggested to make a combination of the known, scissor-like clamps and the clamps with continuously adjustable gripping elements, such as are also known from US Patent No. 2003/0212435 A1.

The surgical instrument that resulted from development was designed according to the invention so as to be disassemblable and reassemblable in three parts in order to keep the opening in the chest free from the surgical instrument required for the operation. The three disassemblable and reassemblable components of the surgical instrument according to the invention advantageously correspond to an operating mechanism, a vascular clamp, and an actuating tool. In other words, the solution of the three tasks for advantageously improving the handling of a disassemblable and reassemblable surgical clamp is reflected in the inventive features described in the claims. The advantageous configurations of the inventive surgical instrument are set forth in the description.

The disassemblable and reassemblable medical instrument is divided into three sections according to the invention, an operating mechanism, a vascular clamp, and an actuating tool. The gripping elements conformed on the gripping mechanism at the distal end of the operating mechanism have a U-shaped construction and extend parallel and separated by a distance determined by the width of the coupling mechanism of the vascular clamp. The inner work surfaces of the gripping elements have a contoured surface, and one shank and one ratchet of the operating device support a guide element arranged thereon, which guide element is formed by a hollow cylinder and has a length approximately corresponding to the total length of one shank including the handle part. The hollow cylinder consists of a metal tube, which is attached to the shank by a thermal process and is completely perforated by a borehole that is used for accommodating, guiding and removing an actuating tool, which is inserted for actuating an adjusting mechanism.

The effect of the surgical instrument's advantageous ability to be disassembled and reassembled thus consists in that it may be assembled before the operation, and disassembled or reassembled during the operation or otherwise while it is being used. Reassembly means that the operating mechanism with the gripping device arranged thereon is able to grasp a vascular clamp, and grip the clamp with the aid of the locking mechanism arranged on the actuating mechanism, thus holding it securely, and that an actuating tool may be inserted through the guide element, which is advantageously arranged on the operating mechanism and consists of a hollow cylinder, to engage with the adjusting mechanism of a vascular clamp.

The actuating tool may advantageously be used at various times. For example, the actuating tool may be inserted through the guide element directly after a vascular clamp has been grasped, in order to adjust the jaws, which represent the working part of the vascular clamp. In another example, however, use of the actuating tool may also be deferred until after the surgical clamp has been inserted through the opening in the body.

The jaws of the vascular clamp may then be closed or opened in measured, stepless manner by rotating the handle of the actuating tool. In order to be able to rotate the actuating tool in the desired direction to open or close the jaws of a vascular clamp, the handle is furnished with markings indicating the respective directions of rotation. A rotation direction marking consists of a legend and a symbol representing an arrow. For the jaw rotating direction, for "Open", for example, the legend reads "OPEN". The symbol of the arrow pointing to the right is located beside the text. This means that when the actuating tool is rotated clockwise, the jaws of the vascular clamp open. To close the jaws, the actuating tool is rotated according to the inscription "CLOSE" with an arrow pointing to the left, that is to say counterclockwise.

Thus, the surgeon is also able to insert the surgical instrument into the opening in the chest without the actuating tool attached, and only push the actuating tool in afterwards, through the guide element arranged on the operating mechanism, until it engages in the adjustment device of the vascular clamp. In the next step, the handle of the actuating tool is turned several times to open the jaws on the vascular clamp to grasp a vessel, for example an aorta. Turning the handle of the actuating tool in the opposite direction causes the jaws to close steplessly and in controlled manner. Closing assures secure occlusion of even sclerotic vessels. Once a vessel is occluded, the actuating tool may be removed or withdrawn from the operating mechanism. In the next step, the locking device is released by unblocking the detent teeth on the ratchets, thereby allowing the operating mechanism to be taken out of the opening in the chest, so that the surgeon is provided with the largest possible opening through which to perform the operation.

An actuating tool thus consists of a cylindrical guide rod that is slightly longer than the length of the hollow cylinder and fits without play in the corresponding bore of the hollow cylinder. A handle with a direction of rotation marking is arranged at one end of the cylindrical guide rod, and a key is arranged on the other end, the key being smaller than the bore in the hollow cylinder.

When the surgical instruments according to the invention are used in open surgical surgical procedures and/or laparoscopic surgical procedures, the vascular clamp that is arranged on the surgical instrument and consists of a working part and an adjustment device may be used for vascular exclusion. Exclusion is assured via the working part, which is equipped for this purpose with two jaws that are specially designed for excluding tube-like vessels of the body, and prevent necrotic destruction of tissue. Avoidance of traumatic damage and secure closure of a vessel or similar tissue to be grasped is assured by implementing variously grooved, toothed and perforated jaw surfaces as described in German utility model DE 2060814. The jaws of a vascular clamp may also be furnished with a groove in the longitudinal direction of the jaw. This arrangement of a groove in the jaws has the advantage that a replaceable padded insert, for example made from thermoplastic elastomer, may be inserted in this groove. A replaceable padded insert of such kind is described for example in U.S. Pat. No. 6,692,514 B2 and U.S. Pat. No. 6,719,766 B1 and US Patent No. 2005/0059987 A1.

When the actuating mechanism is then operated, the locking device is released from the operating mechanism, which causes the gripping elements of the gripping device to open. Opening the gripping device disconnects the vascular clamp from the operating mechanism, and the operating mechanism may also be removed from the opening in the chest. The vascular clamp remains on the occluded body part or vessel. This completes the advantageous disassembly of the surgical instrument into its three component parts. All surgical instrument parts that would block work and vision in the chest opening have been removed. The more vascular clamps and obstructing instrument parts that can be disconnected from their operating mechanisms, the more space remains in the chest opening through which the operation may be carried out, in other words advantageously less of the required access space is obstructed. When the surgical procedure has been completed, the various surgical instruments that are needed and used are removed from the body cavity again. In other words, the catheters, cannulas and clamps that have been inserted are removed through the access opening in the chest.

To remove the vascular clamps according to the invention, the operating mechanism is reattached to a vascular clamp mechanically. For this purpose, the vascular clamp is equipped with a coupling mechanism, which is grasped by a gripping device arranged on the operating mechanism. The grasping action is effected by actuation of the actuating mechanism to move the handle parts together so the gripping elements on the gripping device close until the gripping elements come to rest securely in the coupling area of the vascular clamp that is provided for this purpose. The cooperating detent teeth on the ratchets of the locking device of the operating mechanism prevent the gripping device from coming loose from the vascular clamp. Then, the actuating tool with its key arranged on the cylindrical guide rod is inserted into the bore of the guide element and pushed in as far as the adjustment device, until the key, preferably in a hexagonal wrench shape, engages in the adjusting element of the adjustment mechanism. In this way, the surgical instrument according to the invention is reassembled.

When the key has engaged in the hexagonal socket of the adjusting element, the operator turns the actuating tool on the handle several times to open the jaw and release the vascular clamp from the organic body part. The continuous adjustment mechanism enables controlled release of an occluded vessel. Accordingly, opening and removing the vascular clamp, particularly the aortic clamp, is especially important. The adjusting element of the adjustment mechanism, which functions like a twist-lock system, is designed with a find thread and allows the vascular clamp to be opened in controlled manner, for example to enable a stent to be recovered. After the jaws are opened further, the entire surgical instrument is removed.

The disassemblable and reassemblable surgical instrument according to the invention is constructed so that variously designed vascular clamps, or their variously designed jaws, may be combined with the same operating mechanism and the same actuating tool. Each of the various vascular clamps is furnished with an identical coupling area, which may be grasped by the same corresponding gripping mechanism on the operating mechanism. The adjusting element of the adjustment mechanism on the various vascular clamps is also identical and fits the key on the actuating tool. The capabilities for combining various vascular clamps with a single operating mechanism mean that the number of operating mechanisms for surgical instruments may be reduced advantageously.

Solving the first task consists in developing a continuously adjustable gripping and clamping vascular clamp with a body member, wherein the body member includes a fixed body member I, body element I, and a movable body member II, the push-pull element. The body element is designed to have a working part at the end thereof, preferably a clamping and gripping device. The clamping and gripping device consists of two jaws, wherein one branch is conformed integrally with the distal end of body element I, and is permanently attached thereto, while the other jaw is movably attached to the push-pull element via a pin I, and is arranged so as to be rotatable about this pin, as described in German Patent No. 20 2007 016 057 U1. The jaws are furnished with an advantageous serration, as described in German Patent No. DE 2 060 814 A. Additionally, an adjustment mechanism, a locking mechanism, and a coupling arrangement are arranged on the other, proximal end of the body member, the adjustment mechanism being connected to the locking mechanism via the adjusting element.

In accordance with the invention, the adjustment mechanism is directly joined to the movable jaw, so that the vascular clamp component is shortened considerably. The adjustment mechanism consists of an angled holder, a drive shaft, and an adjusting element, wherein the adjusting element fulfils a dual function. The adjusting element is a part of the adjustment mechanism and also a part of the locking mechanism. This dual function of the adjusting element will be explained in greater detail in the following. The angled holder is of the same width as the fixed body member I and is disposed perpendicularly on the longitudinal axis of body member I and perpendicularly to the longitudinal axis of the push-pull element, and is arranged on the proximal end of body member I. The holder is a geometrically shaped body, preferably a cuboid shape. The cuboid body corresponds to a square rod, which is arranged on the body member and at an angle of 90 degrees thereto. The rod-shaped holder forms an L-shaped assembly together with the body member. The faster includes an aperture, preferably in the form of a borehole. The borehole is arranged in the holder in such manner that the centerline of the aperture is aligned with the centerline of the longitudinal axis of the push-pull element. This means that the centerline of the borehole extends parallel to and at a distance from the centerline of the body member I, and on the same centerline as the threaded hole in the push-pull element.

The borehole serves to accommodate and guide a drive shaft that protrudes from the holder on the right and left. The drive shaft essentially serves as the connecting member between the push-pull element and the adjusting element. One protruding end of the drive shaft, shaft end I, engages in the displaceable push-pull element and the other end of the drive shaft, shaft end II, accommodates an adjusting element. The drive shaft is cylindrical and has three functional areas. Functional area I include a shaft end I, which is constructed as a threaded bolt with a fine thread and engages in the threaded borehole on the movable push-pull element. Functional area II corresponds largely to the middle portion of the drive shaft, and is formed by two flanges located at a distance from one another, to accommodate holder. After the drive shaft has been inserted in the borehole of the holder, the holder is located between the two flanges on the drive shaft, thus providing the drive shaft with a guide. The holder and the flanges are adapted to a fit size according to DIN, for example "H7" (from the shaft/borehole table), such that the drive shaft is guided without play. Finally, functional area III corresponds to the other end of the shaft, shaft end II, which consists of a cylindrical pin and is able to accommodate an adjusting element. For example, the cylindrical pin may also be threaded. Accordingly, there is an aperture on one side of the adjusting element that corresponds to the size and shape of the cylindrical pin. A recess is provided on the opposing side of the adjusting element, which recess has an inner profile for accommodated the actuating tool. The recess is located centrally and is able to accommodate the key of an actuating tool. Now it is possible to move the push-pull element with the key.

In another embodiment, the drive shaft is conformed integrally with the adjusting element. IN the one-piece design, shaft end II with the cylindrical pin is omitted. In order to assemble the adjusting element with the holder, a slot is therefore provided in the holder, which slot corresponds to the borehole and the drive shaft of the adjusting element may be inserted through it. A closing element is provided to close off the slot, and this closing element supports the drive shaft of the adjusting element centrally in the borehole. In principle, the adjusting element resembles the connecting part of a screw. The shaft of a screw corresponds to the cylindrical drive shaft, in this case equipped with special flanges, and the screw head corresponds to the adjusting element, which is specially furnished with a detent profile around the circumference thereof for restraining with a detent spring. An interior shaped element is located centrally in the screw head. The shaped element corresponds to an inner profile, preferably a hexagon socket profile for a positive locking connection with a tool, in this case the key on the actuating tool.

The distal end of the push-pull element is connected rotatably to a pin II, which is arranged in the movable jaw, and the proximal end thereof is connected to the adjusting element. With this arrangement of the two connections on both free ends of the push-pull element, the push-pull element is arranged parallel to the body member and slides along the surface of the body member. When the adjusting element is rotated, the push-pull element moves axially towards the body member, and pin II on the distal end of the push-pull element is also displaced, that is to say it is moved along a circular path. The movable jaw may be opened or closed by displacing the push-pull element. This displacement is effected by rotating the adjusting element. Rotating the adjusting element causes stepless displacement of the jaws. For this purpose, the adjusting element is furnished with a polygonal socket profile, preferably a hexagon socket profile. The hexagon socket profile, also referred to as an Allen key socket, accommodates an actuating tool for adjusting the jaws. The actuating tool enables a vascular clamp according to the invention, or the jaws thereof, to be operated remotely. The jaws are continuously adjustable via a thread, preferably a fine thread, which is provided on the adjusting element, as explained previously, and connects the adjusting element to the push-pull element. This continuous adjustment capability enables the jaws to clamp tissue or a vessel in any position or with any opening angle. The clamping action is assured by the thread on the adjusting element. The thread is self-locking. The continuous adjustment capability of the jaws offers further advantages, which are discussed in German Patent No. DE 20 2007 016 057 U1. One advantage is that the compressive force may be adjusted, so that it may be applied to a tissue or vessel in controlled manner. This in turn provides the capability to control the flow rate of a liquid in the case of a vessel. This means that the operator is able to proceed as gently as possible when dealing with soft tissues, that is to say, to operate atraumatically, and to work more confidently, knowing that the vessel can be sealed mechanically with absolute reliability.

The circumference of the adjusting element is contoured and also functions as a locking means. The contouring around the circumference corresponds to a detent profile, preferably in the form of a grooved profile, which is in contact with a detent spring. The adjusting element is thus not only part of an adjustment mechanism, but also part of a locking mechanism. The locking mechanism thus consists of a detent spring and an adjusting element. The detent spring is made from steel, preferably spring steel, and is secured to the body member. The attachment point for the detent spring is located in the middle of the underside of the body member, that is to say on the reverse side of the holder close to the corner area at the proximal end of the body member. The detent spring is constructed such that it is formed by two legs I, II. The two legs I, II are arranged at an angle to one another and form an angle of about 90 degrees. Leg I serves as horizontal, fixed leg I, and leg II serves as the vertical, movable leg II. Vertical leg II may be deflected in two directions. The deflection is relatively short and may occur clockwise or counterclockwise. The jaws are opened or closed depending on the direction in which the adjusting element is rotated via the actuating tool.

Each rotation of the adjusting element, whether to the left or the right, produces a noise, caused by the movement or deflection of the detent spring. The noise sounds like the click of a ratchet. The click sound is made when the detent spring changes from one groove to the next in the profile, more precisely when the spring is transferred from one groove in the profile to the next groove. The detent spring also cooperates with the transverse grooves in the circumference of the adjusting element to function as a locking means. As a result, body member I of the vascular clamp functions not only as a support for the adjustment mechanism but also as a support for the locking mechanism, According to the invention, a coupling arrangement is located on the opposite of the fixed jaw of the body member. The coupling arrangement is made up of two parts and is arranged on both sides of the body member and the vascular clamp holder. The coupling arrangement is used with the gripping mechanism of the actuating mechanism to grip the vascular clamp of the invention. Like the fixed jaw, the coupling arrangement is conformed integrally with body member II of the vascular clamp. The two gripping elements of the actuating mechanism may be set at a certain distance from each other with a presetting on the ratchets when they are locked in place. The distance between the gripping elements may be selected beforehand such that the actuating tool with its gripping mechanism may be easily slid onto the retaining jaws of the coupling arrangement. In this preselected position, the two gripping elements are approximately parallel with each other. This configuration of the gripping elements and the arrangement of the retaining jaws thus enables the vascular clamp to be easily assembled with the operating mechanism. Each retaining jaw of the coupling arrangement is U-shaped, so that a retaining jaw consists of a contact surface and two guide edges in each case, wherein the guide edges extend in the longitudinal direction of the vascular clamp, and thus also in the longitudinal direction of the body member. The length of the retaining jaws is as important for guiding the gripping elements as the parallel separation of the jaws is for grasping the vascular clamp. The height of the guide edges on the retaining jaws must also be taken into account, as they help to guide the gripper elements properly. The distance between the parallel guide edges is adjusted with respect to the width of the gripping elements to enable simple but secure, precise grasping. The design of the retaining jaws means that the gripping elements of the operating mechanism can only be slid open or grasped in one direction, so that the vascular clamp and the operating mechanism may be attached or assembled quickly and safely. Secure handling of the surgical instrument is thus assured by the design of the gripping elements and the coupling arrangement. Optimal guidance of the gripping elements between the guide edges of the retaining jaws also ensures that the key of an actuating tool may be inserted quickly and safely into the hexagon socket of an adjusting element.

A first component of the object of the invention thus includes a continuously adjustable gripping and clamping, significantly shortened vascular clamp that does not have a scissor-like construction or a bulky ratchet locking system, wherein the vascular clamp includes a body member, a push-pull element, a working part, an adjustment mechanism, a coupling arrangement, and a locking mechanism. The coupling arrangement, which is advantageously configured with the parallel guidance of the retaining jaws, is necessary in order to enable the surgical instrument to be disassembled and reassembled safely and easily. The vascular clamp is advantageously made from a corrosion-resistant steel, preferably stainless steel, titanium or tantalum. In conjunction with an operating mechanism and an actuating tool, the vascular clamp, particularly in the form an aortic clamp for laparoscopic operations on the infrarenal aorta, ensures that even sclerotic vessels may be clamped securely. The twist-lock system with a fine thread enables the vascular clamp to be opened and closed in controlled manner. And the use of replaceable padded inserts on the jaws of the vascular clamp according to the invention enables vessels to be clamped atraumatically.

Solving the second task consists in developing an operating mechanism, wherein the operating mechanism must itself fulfill several tasks. One task is that the operating mechanism must be able to grasp, clamp, guide and correspondingly release a vascular clamp according to the invention. The second task the operating mechanism must perform consists in accommodating an actuating tool practically without play and also to operate this tool. The starting point for development in this context is the disclosed material from the related art. Disclosed material that is available for instance in the documents listed in the background in the related art. In this respect, the Kocher clamp and improvements thereto, such as the medical instrument 600 known from US Patent No. 2003/0212435 A1, is particularly noteworthy. With regard to the operating mechanism from the aforementioned US document, the actuating tool is connected fixedly to the operating mechanism via many individual components, and it obstructs the surgeon's field of vision due to its size. The basis for the operating mechanism according to the invention is therefore a known vascular clamp, consisting of two shanks, connected in scissor-like fashion and movable relative to one another, and having a clamping and gripping device at their distal end, which clamping and gripping device includes two gripping elements, and having a handle mechanism at the proximal end, which includes for example two annular handles, and a locking mechanism close to the annular handles, which locking mechanism has two ratchets furnished with detent teeth on the shank, and with which the gripping elements may be set in one of several positions. The tasks of the operating mechanism according to the invention are very different from those of the vascular clamp. Grasping and controlled clamping of a vessel with the aid of a steplessly adjustable adjustment mechanism is not needed. Accordingly, the solution consists in an operating mechanism for grasping, clamping, and releasing a separate vascular clamp according to the invention, as described in the preceding. Accordingly, the operating mechanism consists of two movable shanks, connected to each other in scissor-like fashion, which are conformed as gripping elements at their distal end, and equipped with handle parts, and also with a locking mechanism having detent teeth near to the handle parts at their proximal end. A shank of the operating mechanism thus supports a guide element arranged thereon, the guide element being permanently fixed to the shank. The guide element serves to accommodate and guide an actuating tool. One free end of the guide element opens directly opposite the adjustment mechanism of the vascular clamp, so that the key of an actuating tool may engage directly in an adjusting element of the adjustment mechanism when inserted therein. The opposite free end of the guide element extends between the two annular handle parts and terminates approximately at the end of the annular handle parts. The gripping mechanism consists of two gripping elements, which are located apart and parallel to each other. The gripping elements are approximately u-shaped, the two legs of the "u" being formed by the two gripping elements. The gripping elements are connected to each other in articulated manner at the apex of the u-shaped configuration. When the clamp is opened wide in the area of the handle parts, the two u-shaped legs of the gripping elements are also open and form a shape roughly resembling a capital "U", the free ends of the legs of which point away from each other, or in opposite directions. When the handle parts are moved towards each other to close the gripping elements until the latches located on the legs of the clamp are touching, the free ends of the two legs also move towards each other, or inwards. In this position, the two gripping elements are parallel to and separated from one another. The separation distance has a specific value. The value is approximately equal to the corresponding value that is fixed by the coupling area on the vascular clamp of the invention. The value of the coupling area corresponds in turn to the dimension resulting from the width of the body member and the two wall thicknesses of the retaining jaws in the coupling area. If the two handle parts are moved closer towards each other, the two opposing ratchets with detent teeth are able to engage with each other, preventing further movement. The cooperating teeth enable the locking arrangement to be set in one of several individual positions. In this way, the force required for clamping a vascular clamp in the gripping mechanism of an operating mechanism may be varied.

The second component of the object of the invention thus includes an operating mechanism, which is constructed in scissor-like fashion, and besides the known annular handles and a known locking arrangement is also equipped with two gripping elements that are shaped such that they are able to grasp and clamp a coupling area of a vascular clamp according to the invention. To enable operation of the adjustment mechanism arranged on a vascular clamp, the operating mechanism is equipped with a guide element that is able to accommodate the actuating tool. The operating mechanism is advantageously made from corrosion-resistant steel, preferably stainless steel, titanium or tantalum. The operating mechanism assures safe handling of a vascular clamp during an operation, and the coupling effect between the vascular clamp and the operating element enables the surgical instrument to be disassembled and reassembled. In other words, the development of the operating mechanism according to the invention is a medical forceps, completely redesigned in a unique form as a gripping and holding forceps. In this medical forceps according to the invention, the operating mechanism is essentially that of a two-legged tool consisting of two handles (handle parts), an articulation, and a pliers head (gripping mechanism) that works according to the lever principle. In this context, two two-sided levers are connected via an articulation, wherein the sides on which the gripping elements are arranged constitute the longer lever arms, and the sides of the pliers head (gripping mechanism) form the shorter lever arms. According to the lever principle, the manual force applied to the handle parts is amplified and transferred to the coupling arrangement via the pliers head (gripping mechanism). The pliers head (gripping mechanism) is furnished with two grasping forceps (gripping elements), the jaws of the pliers head, that is the working surfaces of the gripping elements, are based on the design of a flat-nose pliers. When the pliers head, and thus also the gripping mechanism of the operating mechanism, is in the closed state, the two gripping elements form an open mouth. When the gripping mechanism is in the closed state, the mouth opening is smaller than the width of the coupling arrangement. When the gripping mechanism is open, the mouth opening is much larger than the width of the coupling arrangement.

Solving the third task consists in developing an actuating tool that is capable of acting on an adjustment mechanism of a vascular clamp according to the invention. The adjustment mechanism has already been explained as part of the solution to the first task. A description of the necessary guide for the actuating tool on the operating mechanism is also included in the solution to the second task. Like the two objects of the invention described previously, the actuating member must satisfy the requirement of being able to be disassembled and reassembled. However, the vascular clamps known from the related art are designed as a single part. Even the known aortic clamps manufactured by Eisold Instruments and disclosed in German Patent No. DE 20 2007 016 057 U1, which have an actuating member in the form of a rotatable handle, are not attached to the vascular clamp, nor to the jaws that are to be adjusted, in such a way as to be detachable and reusable. The actuating tool therefore has no connecting elements with the vascular clamp and the operating mechanism, which prevent a surgical instrument from being disassemblable and reassemblable. The actuating tool therefore includes a cylindrical guide rod that fits the corresponding borehole in the guide element. A handle is provided on one end of the guide rod, and a key is arranged on the other free end. The diameter of the key must not be greater than the diameter of the bore in the hollow cylinder of the guide element, instead it must be at least slightly smaller to allow the key to be pushed through easily. The key may be conformed from various known outer profiles. The external profile used on the actuating tool depends on the external profile of the shaped element in the adjusting element of the adjustment mechanism on the vascular clamp. If a slot is provided in the adjusting element to allow a rotating motion, the actuating tool must have a screwdriver key. If the screw head of the adjusting element has a cross slot or Torx profile, the key of the actuating tool must be shaped accordingly. A hexagon socket is preferably used in the screw head of the adjusting element, and a corresponding male hexagon fitting is conformed on the guide rod. It should be noted that the key must not be larger than the diameter of the cylindrical guide rod, because the key must also pass through the guide element.

The third component of the object of the invention thus includes an actuating tool that is equipped with a cylindrical guide rod, which may be fed together with a key arranged thereon through the borehole in a guide element arranged on the operating mechanism, and a handle. With the handle, it is possible to make turning movements that adjust the adjusting element and consequently also adjust the jaws. The actuating mechanism is advantageously made from corrosion-resistant steel, preferably stainless steel, titanium or tantalum. The actuating tool ensures that the jaws of a vascular clamp will be opened and closed safely and reliably, and that the surgical instrument may be disassembled and reassembled during the operation.

It should be noted that the surgical instrument according to the invention may be used quite generally with a large number of different forceps and other clamps with straight or curved clamping legs or jaws of various dimensions, as required by the special applications for which they are employed. In other words, any forceps or clamp that is constructed with a coupling arrangement according to the invention may be converted to a disassemblable and reassemblable instrument with an associated operating mechanism and actuating tool.

An schematic representation of an embodiment of the invention is shown in the drawing, and will be explained in greater detail in the following. In the drawing.

Figure 1:
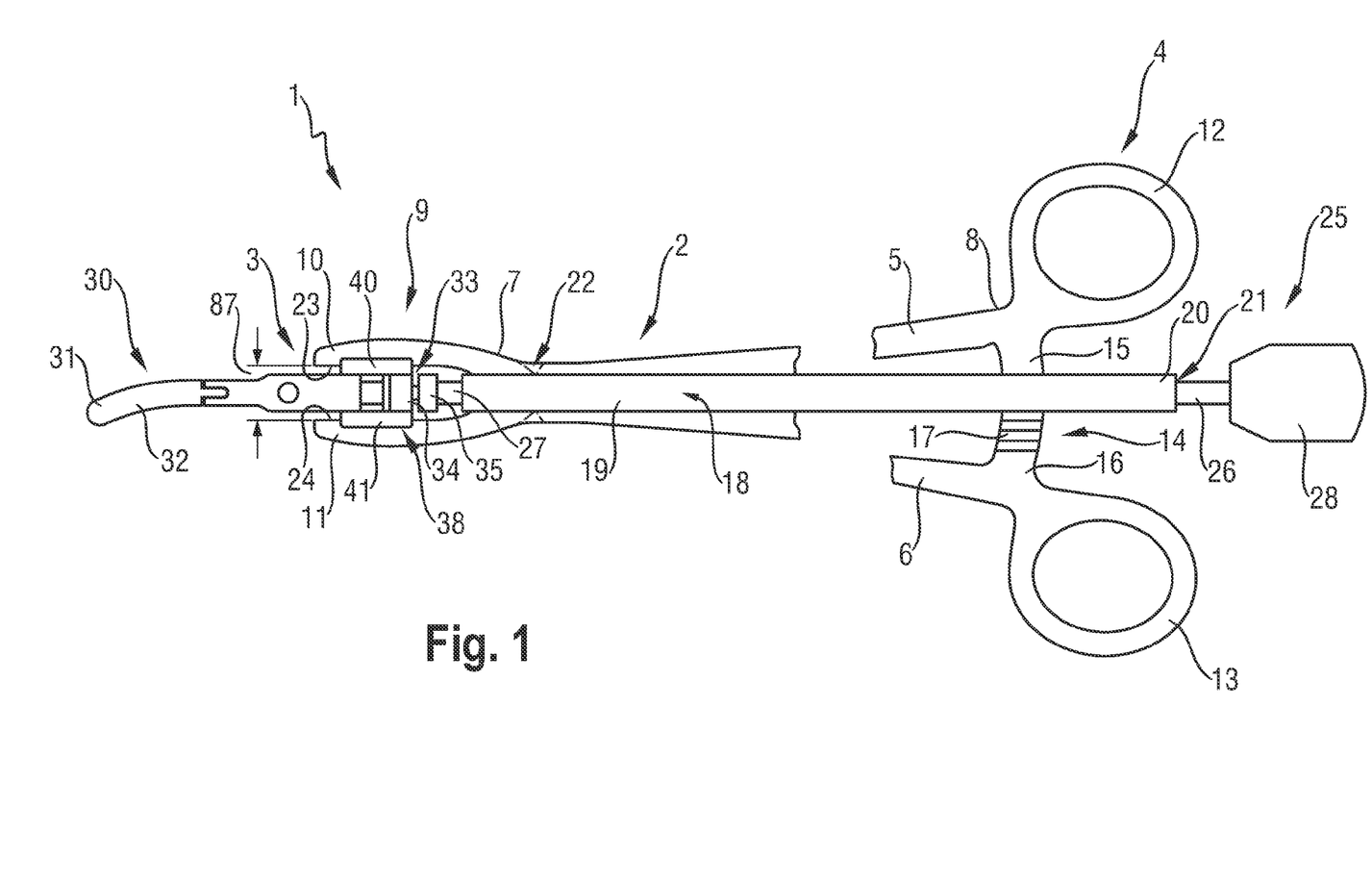
FIG. 1 is a perspective view of an assembled surgical instrument according to the present invention.

The three-part medical instrument according to the invention represented schematically in FIG. 1 essentially consists of an operating mechanism 2 according to the invention, a vascular clamp 3 according to the invention, and an actuating tool 25 according to the invention. The surgical instrument 1 according to the invention satisfies the provisions of the German medical devices act, and the materials used for cleaning make it suitable for sterilization.

The operating mechanism 2 according to the invention has two movable shanks 5, 6, which are connected to each other by a joint in the manner of scissors, and have a gripping mechanism 9 consisting of two gripping elements 10, 11 at their distal end 7, and an actuating mechanism 4 consisting of two handle parts 12, 13 and a locking mechanism 14 close to the handle parts 12, 13 and having two ratchets 15, 16 with detent teeth 17. The handle parts 12, 13 may be of various shapes according to known designs, but the handle parts 12, 13 are preferably realized as annular handles.

One shank 5 of operating mechanism 2 serves to support a guide element 18 that is arranged to thereon. Guide element 18 may be fixed on ratchet 15 of shank 5 both at the distal end 7, and also towards the proximal end 8. Guide element 18 has the form of a hollow cylinder 19, whose length 20 is approximately equal to the total length of a shank 5 with handle part 12 of an operating mechanism 2, and which has a full-length bore 21 that serves to accommodate and guide an actuating tool 25. Hollow cylinder 19 is a corrosion-resistant metal tube, preferably made from stainless steel, and is fixed to shank 5 and on ratchet 15 by a thermal process, preferably laser welding. Alternatively, guide element 18 may also be laser welded only to the ratchet 15 arranged on shank 5, or only to shank 5.

Figure 2:
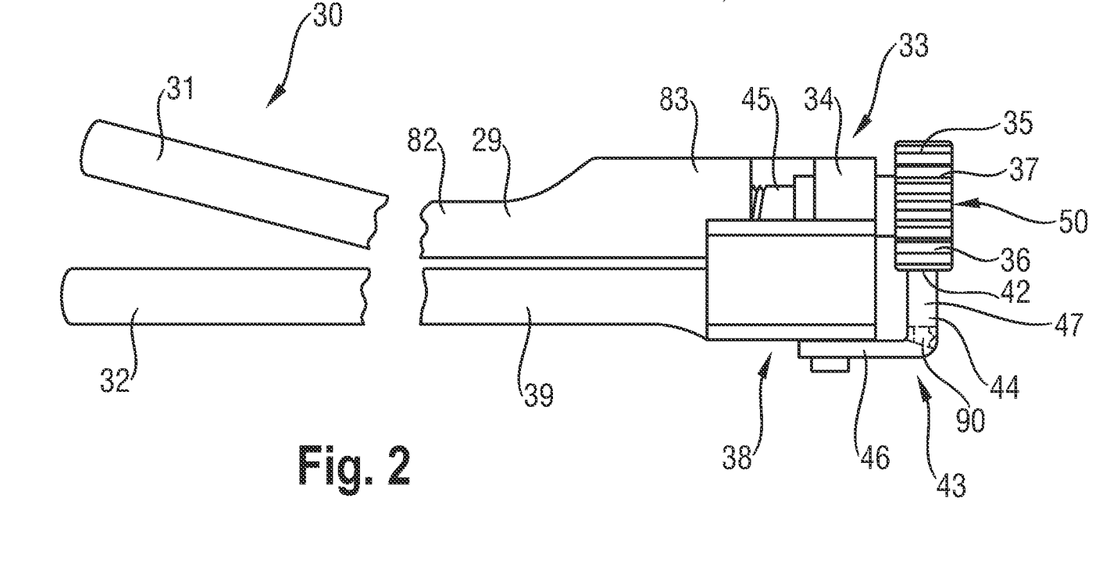
FIG. 2 is a side view of an embodiment of a vascular clamp according to the invention.
Figure 2A:
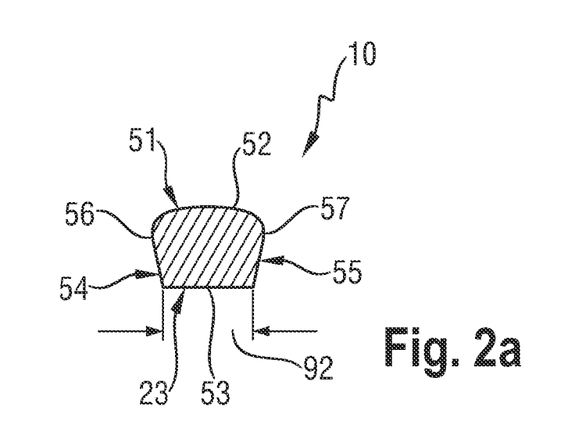
FIG. 2a is a cross section of an embodiment of a gripping element according to the invention.

Gripping mechanism 9 consists of two gripping elements 10, 11, which extend approximately parallel and at a distance from each other. In their parallel position, gripping elements 10, 11 form a rough u-shape, wherein the two long legs of the "U" are formed by the two gripping elements 10, 11. If operating mechanism 2 on actuating mechanism 4 opened, gripping elements 10, 11 also open and the mouth of the "U" also becomes wider. When actuating mechanism 4 is closed, that is to say when handle parts 12, 13 are moved closer together, the long legs of the "U" are moved, thus also moving the two gripping elements 10, 11 closer together. Thus, gripping elements 10, 11 may only be moved closer together until the opening of the "U" between the two long legs and thus also between the two gripping elements 10, 11 has been reduced by a certain value. This value for reducing the opening of the "U" corresponds to the force that may be applied to parallel and separate retaining jaws, 40, 41 via operating mechanism 2 (see FIG. 4) of coupling arrangement 38 in order to grasp and hold vascular clamp 3 securely. Once an operating mechanism 2 has been coupled with a vascular clamp 3, however, gripping elements 10, 11 are not able to exceed a parallel position or distance 87 relative to one another. The position of gripping elements 10, 11 is determined on the basis of the parallel distance between the two retaining jaws 40, 41 of coupling arrangement 38. Gripping elements 10, 11 are connected to each other in articulated manner at the apex (of joint 22) of the u-shaped configuration. As is shown in FIG. 2a, inner working surfaces 23, 24 of gripping elements 10, 11 have a contoured surface. The contour of the surface may have a grooved, toothed, perforated or knurled profile. The contouring of working surfaces 23, 24 ensure a reliable clamping action between vascular clamp 3 and operating mechanism 2. The shape of a gripping element 10, 11, or the shape of the jaws of a gripping element 10, 11, is designed to approximately resemble the shape of the jaws of a flat-nose pliers. Gripping elements 10, 11 are prolonged and are tapered towards the end, while the cross section of a gripping element 10, 11 is essentially a square with a circular segment on one side, so that this side of gripping element 10, 11 has a spherical outer side 51. This spherical outer side 51 of a gripping element 10, 11 is essential in view of the risk of injury to the patient. The side opposite the circular segment or spherical surface 52 of outer side 51 corresponds to working surface 23, 24, which is flat on one side and has a serration 53 on the other side. The two parallel and separate lateral surfaces 54, 55, each of which adjoins working surface 23, 24 at an angle of 90 degrees, form guiding sides 56, 57 of gripping elements 10, 11. Guide surfaces 54, 55 may advantageously taper by a few degrees towards working surface 23, 24, which lends the cross section of a gripping element 10, 11 a shape approximately resembling an inverted trapezoid. Corresponding to the sloped guide surfaces 54, 55 of gripping elements 10, 11, inner guide surfaces 61, 62 of retaining jaws 40, 41 are also inclined. This inclination corresponds to a tapering of inner guide surfaces 61, 62 towards contact surface 48, 49 of base wall 58. Guide sides 56, 57 of gripping elements 10, 11 cooperate with inner guide surfaces 61, 62 of fillets 59, 60 (see also FIG. 4) to assure the guidance and centering of vascular clamp 3. Because vascular clamp 3 is well centered by operating mechanism 2, these two components are positioned optimally with respect to each other, so that actuating tool 25 is correctly aligned for a connection with adjusting element 35. The relatively long retaining jaws 40, 41 conformed on body member 39 and the guide elements arranged on the retaining jaws 40, 41 and gripping elements 10, 11 prevent vascular clamp 3 from tilting in coupling arrangement 38 after they have been closed. It is thus impossible for vascular clamp 3 to tilt between gripping elements 10, 11 of operating mechanism 2. This advantageous embodiment of coupling arrangement 38 and the advantageous embodiment of gripping mechanism 9 is an important feature for ensuring safe handling when the surgical instrument 1 according to the invention is being used.

Figure 3:
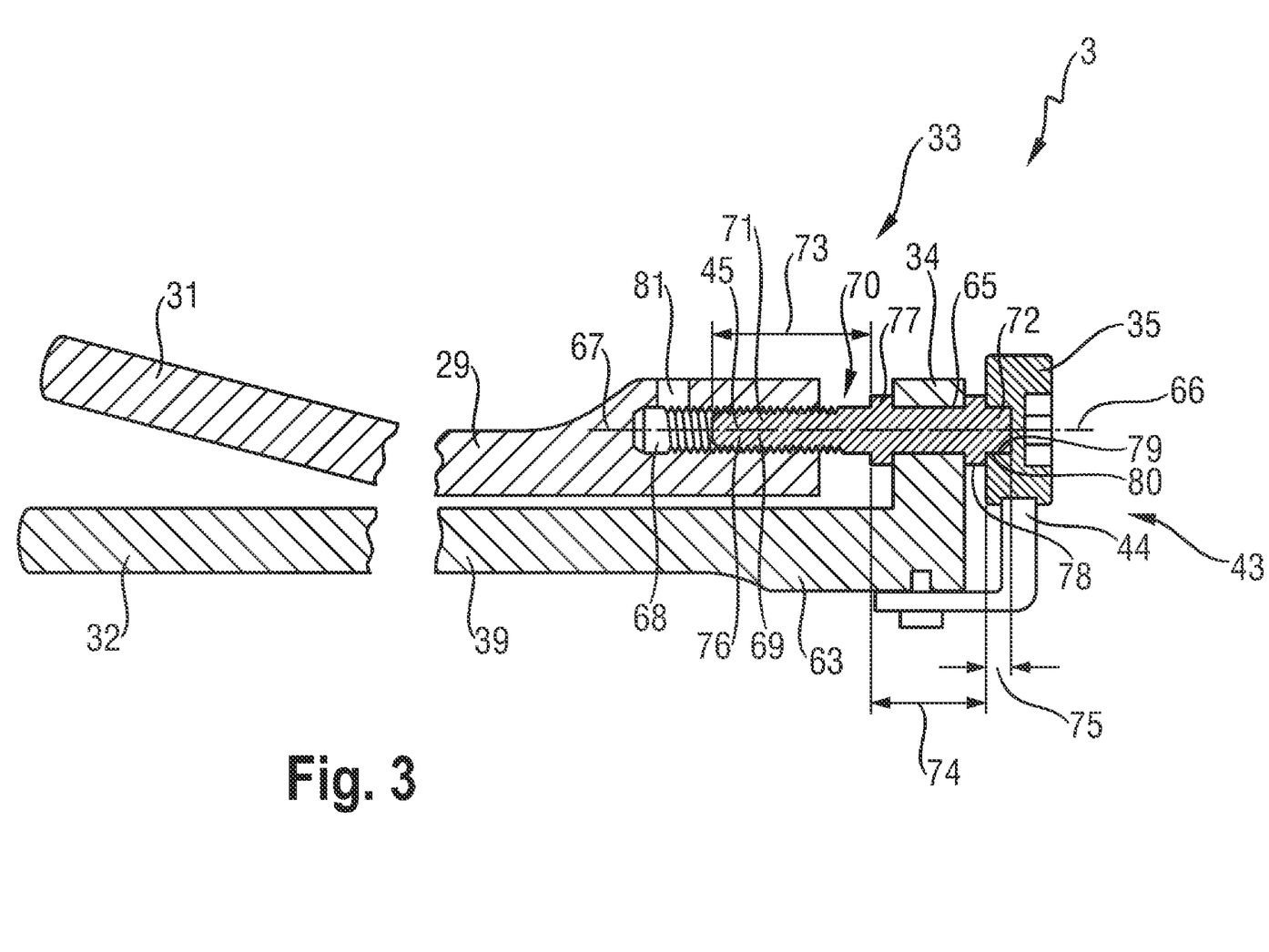
FIG. 3 is a sectional view of an embodiment of a vascular clamp of the invention, in accordance with FIG. 2 and in accordance with the present invention.
Figure 4:
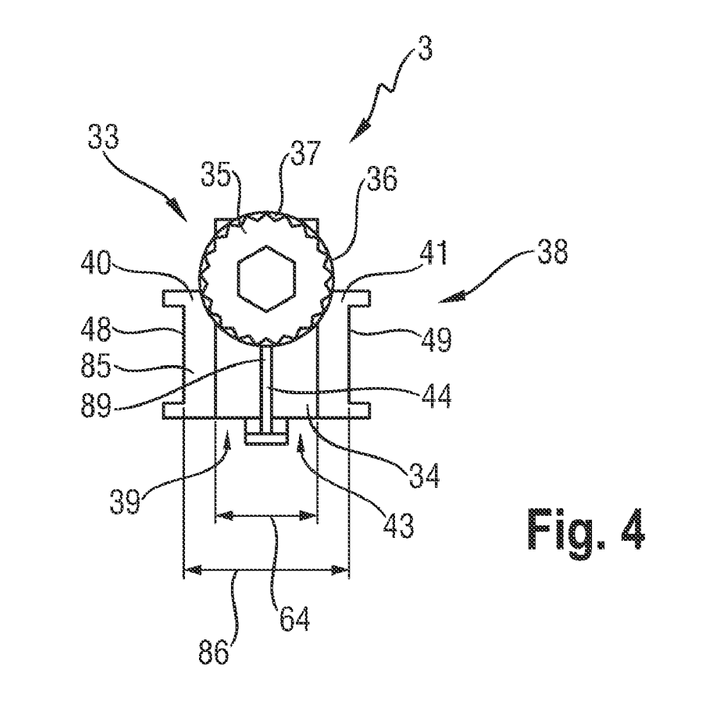
FIG. 4 is a front view of an embodiment of a vascular clamp according to the invention.

FIG. 1 also shows that actuating mechanism 4 is in a locked position. In the locked position, detent teeth 17 of ratchets 15, 16 cooperate, and gripping elements 10, 11 of gripping mechanism 9 enclose a vascular clamp 3 in the area of coupling arrangement 38. Vascular clamp 3 includes an working part 30, an adjustment mechanism 33, and a coupling arrangement 38. Working part 30 is formed by two jaws 31, 32, adjustment mechanism 33 consists of a holder 34 and an adjusting element 35. Coupling arrangement 38 consists of two retaining jaws 40, 41, which are arranged laterally in the area of adjustment mechanism 33. FIGS. 2, 3 and 4 show the vascular clamp 3 of the invention in greater detail. Gripping elements 10, 11 of gripping mechanism 9 have clamped vascular clamp 3 firmly between them with retaining jaws 40, 41 of coupling arrangement 38. Jaws 31, 32 of vascular clamp 3 are also closed. An actuating tool 25 must be used to open jaws 31, 32.

Actuating tool 25 consists of a cylindrical guide rod 26, a key 27 and a handle 28. Cylindrical guide rod 26 is slightly longer than hollow cylinder 19 and the diameter of cylindrical guide rod 26 is adapted to within a few millimeters, preferably 5 mm, to fit the corresponding bore 21 of hollow cylinder 19. An ergonomically designed handle 28 is arranged on one end of cylindrical guide rod 26 for rotating actuating tool 25. Handle 28 consists of a metal hollow body which, like the entire actuating tool 25, is suitable for sterilization in the cleaning process. At the other end of cylindrical guide rod 26 there is a key 27. Key 27 may have various known tool configurations. For example, it may have the shape of straight blade, a cross slot blade, an Allen key blade, or a Torx blade. It is preferably conformed as an external polygon, particularly for an Allen head screw. In the preferred design, actuating tool 25 thus forms a special screwdriver with an Allen key shape for a surgical instrument 1. Key 27 may be fixed to cylindrical guide rod 26, or advantageously connected therewith as a single part. Key 27 must not be larger than the size of bore 21 in hollow cylinder 19, instead it is advantageously slightly smaller.

In the example of FIG. 1, the object of the invention shown is an assembled surgical instrument 1, preferably realized as an aortic clamp, consisting of three parts. As described previously, three-part surgical instrument 1 may be easily and repeatedly disconnected between vascular clamp 3, operating mechanism 2 and actuating tool 25, and reassembled. The vascular clamp 3 component is used as a simple, forceps-like surgical instrument 1 that uses a mechanical operation between its jaws 31, 32 to compress and clamp tissues or vessels. Clamping action is applied by the pressure of jaws 31, 32, which is produced by the rotating motion of adjusting element 35. An actuating tool 25 is used to produce the rotating motion at adjusting element 35. After each rotating motion at actuating tool 25, a locking action for jaws 31, 32 is present, see the notes on FIG. 2 for a an explanation of this.

FIG. 2 is a diagrammatic side view of an embodiment of a vascular clamp 3 according to the invention, and FIG. 2a shows a cross section of gripping element 10, 11.

The basic element of vascular clamp 3 is a body member 39, and it also consists essentially of a working part 30, an adjustment mechanism 33, a locking mechanism 43 and a coupling arrangement 38. Working part 30 is formed by two jaws 31, 32, wherein the end of one jaw 32 opposite the free end extends as a single part from one end of body member 39 and is permanently connected thereto. On the other hand, the other jaw 31 is connected to push-pull element 29 via a pin (not shown) and is arranged so as to be movable about a pin of push-pull element 29. A holder 34 integral with and protruding from body member 39 is located on the other end of body member 39, facing the rear side of jaw 32. Together with adjusting element 35, holder 34 forms an adjustment mechanism 33. Holder 34 is arranged perpendicularly to the longitudinal axis of body member 39 and perpendicularly to the longitudinal axis of push-pull element 29, wherein holder 34 is realised as a geometric shape, preferably a rectangular rod that is arranged on and at an angle of 90 degrees with respect to body member 39. Rod-shaped holder 34 creates an L-shaped structure with body member 39 and accommodates adjusting element 35. Some of the reference numbers listed hereafter are shown in FIG. 3. Holder 34 includes an opening 65, preferably realised as a borehole, for this purpose. Opening 65 is arranged in holder 34 in such manner that midline 66 of opening 65 is aligned with midline 67 of the longitudinal axis of push-pull element 29. Push-pull element 29 is connected at its distal end 82 to movable jaw 31 via a pin II (not shown), which is arranged in the jaw, and at its proximal end 83 to adjusting element 35. By this arrangement of the two connections at both free ends of push-pull element 29, push-pull element 29 is located parallel to body member 39 and is able to slide over the surface of body member 39. When adjusting element 35 is rotated, push-pull element 29 is displaced axially towards body member 39, and pin II on distal end 82 of push-pull element 29 also moves, that is to say it is displaced along a circular path. The displacement of push-pull element 29 thus allows movable jaw 31 to be opened or closed. Displacement is effected rotating adjusting element 35. Rotating adjusting element 35 causes jaw 31 to be adjusted steplessly. For this, adjusting element 35 has a hexagon socket profile 50. Hexagon socket profile 50 accommodates an actuating tool 25 (see FIG. 1) for adjusting jaw 31. Actuating tool 25 may be used to operate the vascular clamp 3 of the invention, or its jaw 31, remotely. Jaw 31 is adjusted steplessly via a fine thread 76 (see FIG. 3), which, as explained previously, is arranged on adjusting element 35 and connects adjusting element 35 to push-pull element 29. The embodiment of the connection between push-pull element 29 and adjusting element 35 may be seen in FIG. 3.

Adjusting element 35 is essentially constructed in two parts, a screw head section 36 and a screw shank section 45. Both parts are assembled to form a permanently joined part, an inseparable adjusting element 35. In a different design, screw head section 36 and screw shank section 45 of adjusting element 35 are constructed as a single part. Holder 34 of adjustment mechanism 33 is located between screw head section 36 and screw shank section 45. Screw shank section 45 is furnished with at least one flange I 77, II 78 and a fine thread 76 (see figure), the effect of which is to ensure a self-locking action in threaded hole 68 of push-pull element 29. Screw shank section 45 thus engages in push-pull element 29. Screw head section 36 of adjusting element 35 has a hexagon socket 50 (see FIG. 4) and a detent profile 37 on its circumference. Detent profile 37 is made up of transverse grooves, preferably grooves in the form of involute teeth, in which a detent spring 44 engages. Detent spring 44 is arranged below body member 39. Detent spring 44 may be attached to body member 39 in various ways. Advantageously, detent spring 44 is riveted in place, a threaded connection is also conceivable. Detent spring 44 is configured in such manner that it is formed by two legs I, II 46, 47. The two legs I, II 46, 47 are arranged at an angle to one another, and an angle of approximately 90 degrees is formed between them.

Accordingly, vertical shank II 47 of detent spring 44 extends parallel to and at a distance from holder 34, and the thin engaging edge 42 of detent spring 44 also extends parallel to holder 34. In this position, engaging edge 42 of vertical shank II 47 cannot engage in the transverse grooves of detent profile 37. Therefore, vertical shank II 47 must be rotated through 90 degrees. With a s rotation through 90 degrees, the parallel distance between vertical shank II 47 and holder 34 is retained, but engaging edge 42 moves to a different position. The rotation of vertical shank II 47 is performed very close to the angle formed between the two shanks I 46, II 47, by twisting vertical shank 47. After twisting 90, engaging edge 42 of vertical shank II 47 extends parallel to transverse grooves 37 in adjusting element 35. Meanwhile, shank I 46 forms horizontal fixin shank I 46, and shank II 47, which is the vertical, movable shank II 47, is able to be deflected in two directions. This deflection is relatively short and may occur either clockwise or counterclockwise, depending on the direction of rotation required to open or close jaws 31, 32 via adjusting element 35, using actuating tool 25. Detent spring 44 and adjusting element 35 together form a locking mechanism 43.

FIG. 3 shows a cutaway view of an embodiment of a vascular clamp 3 according to the invention. This sectional view shows bearing body member 39 with the constructions according to the invention of adjustment mechanism 33 and locking mechanism 43. The reference numbers shown in FIG. 2 are used similarly here, but are not further described.

Holder 34, arranged on proximal end 63 of body member 39, is clearly visible. Holder 34 is constructed in a geometric shape, preferably a cuboid body. The cuboid body corresponds to a rectangular rod, which is arranged on body member 39 and at an angle of 90 degrees thereto. Rod-shaped holder 34 forms an L-shaped assembly together with body member 39. Holder 34 has the same width 64 (see also FIG. 4) as fixed body member 39, and is positioned perpendicularly on the longitudinal axis of body member 39 and perpendicularly to the longitudinal axis of push-pull element 29. Holder 34 includes an opening 65, preferably in the form of a borehole. Borehole 65 is applied to holder 34 in such manner that midline 66 of opening 65 is aligned with midline 67 of the longitudinal axis of push-pull element 29. This means that midline 66 of borehole 65 extends parallel and at a distance from the midline of body member 39 and on the same midline 67 as threaded hole 68 in push-pull element 29.

Borehole 65 serves to accommodate and guide drive shaft 69, which protrudes from holder 34 on the right and left. Drive shaft 69 essentially serves as the connecting element 70 between push-pull element 29 and adjusting element 35. One protruding shaft end I 71 of drive shaft 69 engages in displaceable push-pull element 29, and the other shaft end II 72 accommodates an adjusting element 35. Drive shaft 69 is cylindrical and has three functional areas I, II, III. Functional area I 73 includes shaft end I 71, which is constructed as a screw shank section 45 with fine thread 76 and engages in threaded borehole 68 in displaceable push-pull element 29. Functional area II 74 corresponds largely to the middle portion of drive shaft 69, which is formed by two flanges I 77, II 78 located at a distance from one another, and between which holder 34 is located. After drive shaft 69 has been inserted in borehole 65 of holder 34, holder 34 is located between the two flanges I 77 and II 78 on drive shaft 69, thus serving as a guide for drive shaft 69. Holder 34 and flanges I 77 and II 78 are adapted to fit each other. This adaptation is based on a DIN. The DIN specifications include a size tolerance, for example for "H7", which may be reviewed in a table entitled "Shaft/borehole". This closely toleranced fitting dimension enables flanges 77, 78 of drive shaft 69 to guide holder 34 between them without play. Finally, functional area III 75 corresponds to the other shaft end II 72, and is formed by a cylindrical pin 79 and is able to accommodate an adjusting element 35. For example, cylindrical pin 79 may also be threaded. Accordingly, in its two-piece construction, adjusting element 35 is furnished with an aperture 80 on one side, which corresponds to the size and shape of cylindrical pin 79. In the one-piece construction, drive shaft 69 protrudes from adjusting element 35, so there is no need to provide an aperture 80 in adjusting element 35.

It is also advantageous to note a cleaning orifice 81, which is provided at the end of threaded hole 68 in push-pull element 29. Threaded hole 68 is a blind hole and is therefore very difficult to clean. In order to comply fully with the regulations for sterilization conditions, a cleaning orifice 81 that communicates with threaded hole 68 is located at the end of the blind hole. Cleaning orifice 81 is located on the top of push-pull element 29 and extends parallel to midline 67 of threaded hole 68. Adjustment mechanism 33 has been referred to previously, with reference to FIG. 2, and will be explained in greater detail in the notes on FIG. 4.

Figure 4A:
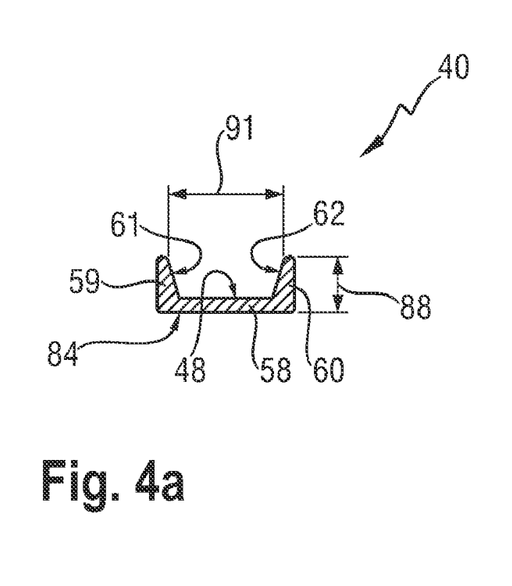
FIG. 4a is a cross section of an embodiment of a retaining jaw according to the invention.

FIG. 4 shows a front view of an embodiment of a vascular clamp 3 according to the invention, and FIG. 4a shows a retaining jaw 40, 41 from coupling arrangement 38, which is arranged on vascular clamp 3.

The front view in FIG. 4 shows body member 39 with coupling arrangement 38, adjustment mechanism 33 and locking mechanism 43. Coupling arrangement 38 consists of two retaining jaws 40, 41, which are connected in a single piece with proximal end 63 of body member 39 (see FIG. 3) of vascular clamp 3 and are arranged laterally in the longitudinal direction on body member 39. Each retaining jaw 40, 41 has a u-shaped cross-sectional profile (see FIG. 4a). A u-shaped retaining jaw 40, 41 is formed from a base wall 58 and two parallel and separate fillets 59, 60. Outer wall 84 of base wall 58 is connected to body member 39. This means that the outer wall 84 is the side facing towards body member 39, and the inner surface thereof serves at the contact surface 48, 49 for gripping elements 10, 11. The free ends of fillets 59, 60 point away from body member 39. The inner surfaces of fillets 59, 60 serve as guide surfaces 61, 62, which are separated by a given distance 91, which distance corresponds to the distance between guiding sides 56, 57, which in turn is determined by the width 92 (see FIG. 2a) of gripping elements 10, 11. The inner surface of base wall 58 serves as contact surface 48, 49. Advantageously, both contact surfaces 48, 49 of retaining jaws 40, 41 are parallel and located at distance from one another. The parallel distance is determined by the width 64 of body member 39 and the wall thickness 85 of the two retaining jaw 40, 41, which yields a certain value X or a certain width 86 in mm for coupling arrangement 38. Value X for coupling arrangement 38 is preferably in the range from 10 mm to 20 mm, depending on the width 64 of body member 39 of a vascular clamp 3. With this value X in mm, gripping elements 10, 11 of gripping mechanism 9 are also located parallel with a distance therebetween. Accordingly, parallel distance 87 (see FIG. 1) between gripping elements 10, 11 is adapted to the width 86 of coupling arrangement 38. In order to prevent gripping elements 10, 11 from slipping off of contact surfaces 48, 49 of retaining jaws 40, 41, contact surfaces 48, 49 have a contoured surface. The contouring of contact surfaces 48, 49 may match that of the inner working surface 23, 24 of gripping elements 10, 11, which in turn increases the friction between jaws 31, 32 a retaining jaws 40, 41.

In a further embodiment (not shown) of the guide elements in coupling arrangement 38 and in gripping mechanism 9, it is not the contact surfaces 48, 49 of retaining jaws 40, 41 that engage with the working surfaces 23, 24 of gripping elements 10, 11, but instead only guide surfaces 61, 62 of retaining jaw 40, 41 with guiding sides 56, 57 of gripping elements 10, 11. In this configuration, fillets 59, 60 of retaining jaws 40, 41 are designed with considerably greater height 88. Guide surfaces 61, 62 of retaining jaws 40, 41 and guide surfaces 54, 55 are furnished with a surface structure to prevent gripping element 10, 11 and operating mechanism 2 from slipping out of coupling arrangement 38, and most importantly to enable vascular clamp 3 to be grasped under perfect control.

Adjusting element 35 of adjustment mechanism 33, with toothed detent profile 37 on the circumference of screw head 36 is clearly visible. In order to lock jaws 31, 32, free end 89 of detent spring 44 engages in detent profile 37. Detent spring 44 is fixed to body member 39 below holder 34. On the other hand, adjusting element 35 is located on shaft end II 72 of drive shaft 69, which is retained in holder 34. Inner shaped element, consisting of a hexagon socket 50 for introducing key 27 of actuating tool 25, is visible in screw head section 36 of adjusting element 35.

Legend

| | |
|---|---|
| 1 | Surgical instrument |
| 2 | Operating mechanism (v.1) |
| 3 | Vascular clamp (v.1) |
| 4 | Actuating mechanism (v.2) |

-continued

| | |
|---|---|
| 5 | Shank (v.2) |
| 6 | Shank (v.2) |
| 7 | Distal end (v.2) |
| 8 | Proximal end (v.2) |
| 9 | Gripping mechanism (v.2) |
| 10 | Gripping element (v.2) |
| 11 | Gripping element (v.2) |
| 12 | Handle part (v.2, 5) |
| 13 | Handle part (v.2, 5) |
| 14 | Locking mechanism (v.2) |
| 15 | Ratchet (v.2, 5) |
| 16 | Ratchet (v.2, 6) |
| 17 | Detent teeth (15, 16) |
| 18 | Guide element (v.2) |
| 19 | Hollow cylinder (v.18) |
| 20 | Length (v.19) |
| 21 | Bore (v.19) |
| 22 | Joint (v.2, 5, 6) |
| 23 | Working surface (v.10) |
| 24 | Working surface (v.11) |
| 25 | Actuating tool (v.1) |
| 26 | Cyl. guide rod (v.25) |
| 27 | Key (v.25) |
| 28 | Handle (v.25) |
| 29 | Push-pull element (v.3) |
| 30 | Working part (v.3) |
| 31 | Jaw (v.3) |
| 32 | Jaw (v.3) |
| 33 | Adjustment mechanism (v.3) |
| 34 | Holder (v.33, 39) |
| 35 | Adjusting element (v.33, 43) |
| 36 | Screw head section (v.35) |
| 37 | Detent profile (v. 33, 35) |
| 38 | Coupling arrangement (v.3) |
| 39 | Body member (v.3) |
| 40 | Retaining jaw (v.38) |
| 41 | Retaining jaw (v.38) |
| 42 | Engaging edge (v.44) |
| 43 | Locking mechanism (v.3) |
| 44 | Detent spring (v.43) |
| 45 | Screw part (v.33, 35) |
| 46 | Leg I (v.44) |
| 47 | Leg II (v.44) |
| 48 | Contact surface (v.40) |
| 49 | Contact surface (v.41) |
| 50 | Hexagon socket (v.33) |
| 51 | Outer side (v.10, 11) |
| 52 | Spherical surface (v.10, 11) |
| 53 | Serration (v.10, 11) |
| 54 | Lateral surface (v.10, 11) |
| 55 | Lateral surface (v.10, 11) |
| 56 | Guiding side (v.10, 11) |
| 57 | Guiding side (v.10, 11) |
| 58 | Base wall (v. 40, 41) |
| 59 | Fillet (v. 40, 41) |
| 60 | Fillet (v.40, 41) |
| 61 | Guide surface (v.40, 41) |
| 62 | Guide surface (v.40, 41) |
| 63 | Proximal end (v.39, 3) |
| 64 | Width (v.34, 39) |
| 65 | Opening (v.34) |
| 66 | Centreline (v.65) |
| 67 | Centreline (v.68) |
| 68 | Threaded hole (v.29) |
| 69 | Drive shaft (v.33) |
| 70 | Connecting element (v.33) |
| 71 | Shaft end I (v.69) |
| 72 | Shaft end II (v.69) |
| 73 | Functional area I (v.69) |
| 74 | Functional area II (v.69) |
| 75 | Functional area III (v.69) |
| 76 | Fine thread (v.69) |
| 77 | Flange I (v.69) |
| 78 | Flange II (v.69) |
| 79 | Cylindrical pin Zapfen |
| 80 | Opening (v.35) |
| 81 | Cleaning orifice (v.68) |
| 82 | Distal end (v.29) |
| 83 | Proximal end (v.29) |
| 84 | Outer wall (v.40, 41) |
| 85 | Wall thickness (v.40, 41) |
| 86 | Width (v.38) |
| 87 | Distance (v.10, 11) |
| 88 | Height (v.59, 60) |
| 89 | Free end (v.44) |
| 90 | Twist (v.44) |
| 91 | Distance (v.40, 41) |
| 92 | Width (v.10, 11) |

The invention claimed is:

1. A medical instrument for occluding tube-like body parts, comprising:
  a vascular clamp further comprising:
    a body member;
    a push-pull element
    a coupling arrangement having first and second retaining jaws, said coupling arrangement having a width;
    an adjusting mechanism having an angled holder, a drive shaft, and an adjusting element; and
    a first locking mechanism, said first locking mechanism comprising a detent spring and said adjusting element;
  an operating mechanism, said operating mechanism being constructed and arranged for placing said vascular clamp in a user selected location in a patient during surgery, said operating mechanism further comprising:
    first and second shanks movably connected with one another in a scissor-like manner;
    a gripping mechanism operable for engaging said vascular clamp and being releasable from said vascular clamps, said gripping mechanism arranged at a distal end of said first and second shanks and having first and second gripping elements, said first and second gripping elements being U-shaped and parallel with respect to one another and separated from one another by distance substantially equal to said width of said coupling arrangement when said gripping elements are in a closed position;
    first and second handle parts arranged at a proximal end of said first and second shanks;
    a second locking mechanism arranged at said proximal end of said first and second shanks operable to fix said first and second handle parts in position relative to one another; and
    a guide element comprising a hollow cylinder connected at a first end to one of said first and second shanks at said distal end of said shank and at second end to said proximal end of said first or second shank, said guide element being fixed in position relative to said first or second shank to which said guide element is connected;
  an actuating mechanism, said actuating mechanism arranged for insertion through said guide element and further comprising:
    a guide rod;
    an actuator handle at a proximal end of said guide rod;
    a key at a distal end of said guide rod, said key being engagable and disengagable with said adjusting mechanism on said vascular clamp;
  wherein said operating mechanism, said vascular clamp, and said actuating mechanism are each disassembleable from each other and reassembleable with each other, including during operation on a patient.

2. The medical instrument as set forth in claim 1, wherein said angled holder has a width substantially similar to said body member and is arranged on a proximal end of said body member, substantially perpendicular to a longitudinal axis of said body member and substantially perpendicular to said push-pull element, said angled holder comprising a cuboid body having a borehole, said borehole engaging said drive shaft, and wherein said drive shaft further comprises a first shaft end engaged with said push-pull element and a second shaft end engaged with said adjusting element.

3. The medical instrument as set forth in claim 1, wherein said first and second retaining jaws are attached to said body member and are arranged on a proximal end of said vascular clamp and laterally in a longitudinal direction on said body member, wherein said first and second retaining jaws are parallel and separated by a width of the body member.

4. The medical instrument as set forth in claim 3, wherein each of said first and second retaining jaws comprises a U-shaped cross section and includes a base wall and first and second separate and parallel fillets, wherein an inner surface of said base wall forms a contact surface for one of said first and second gripping elements.

5. The medical instrument as set forth in claim 4, wherein each of said first and second fillets have an interior guide surface, each of said interior guide surfaces having a tapering profile towards said contact surface, wherein a slope of said guide surfaces corresponds to a tapering slope of lateral surfaces of said gripping elements.

6. The medical instrument as set forth in claim 1, wherein said second locking mechanism further comprises ratchets with detent teeth, said ratchets and teeth providing for said gripping elements to be positioned in one of several user selected positions.

7. The medical instrument as set forth in claim 1, wherein said drive shaft further comprises first and second ends with a threaded bolt section at said first end, first and second flanges, said first and second flanges intermediate said first and second ends and being longitudinally spaced from one another, wherein said angled holder engages said drive shaft between said first and second flanges after assembly, and a cylindrical pin at said second end.

8. The medical instrument as set forth in claim 1, wherein said detent spring is arranged on said body member opposite said angled holder, said detent spring further comprising first and second sections oriented at a right angle to one another, wherein said first section is connected to said body member and said second section engages said adjusting element.

9. The medical instrument as set forth in claim 1, wherein said adjusting element further comprising a screw head section, wherein a circumference of said screw head section comprises a detent profile for engagement with said detent spring, and wherein said screw head section further comprises an internal shaped element for engagement with said key.

10. The medical instrument as set forth claim 1, wherein said key comprises a profile selected from the group consisting of a male hexagon fitting, a male cross slot profile, or a male Torx profile.

11. The medical instrument as set forth in claim 1, wherein said guide element has a length substantially equivalent to a total length of said first or second shank including said handle part.

12. The medical instrument as set forth in claim 1, wherein said guide element is connected to said first or second shank by a thermal process.

13. The medical instrument as set forth in claim 1, wherein said actuator handle further comprises a rotation direction marking.

\* \* \* \* \*

UNITED STATES PATENT AND TRADEMARK OFFICE
CERTIFICATE OF CORRECTION

PATENT NO. : 8,409,229 B2
APPLICATION NO. : 12/728834
DATED : April 2, 2013
INVENTOR(S) : Wolfgang Wiedenbein It is certified that error appears in the above-identified patent and that said Letters Patent is hereby corrected as shown below:

In the Specification

Col. 7, line 2, delete "fulfils" and replace with -- fulfills --

Signed and Sealed this
Sixteenth Day of July, 2013

Teresa Stanek Rea
*Acting Director of the United States Patent and Trademark Office*